US00PP09731P

United States Patent [19]

Dummen

[11] Patent Number: Plant 9,731

[45] Date of Patent: Dec. 3, 1996

[54] GERANIUM PLANT NAMED 'HWD FUEGA'

[75] Inventor: Günter Dümmen, Rheinberg-Eversael, Germany

[73] Assignee: Dummen Jungpflanzenkulturen, Rheinberg-Eversael, Germany

[21] Appl. No.: 521,403

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of Geranium plant named HWD Fuega, characterized by its semi-double rubine red flowers; large umbels; large flowers; compact plant size; dark green leaves; and early flowering.

1 Drawing Sheet

The present invention relates to a new and distinct cultivar of Geranium plant, botanically known as *Pelargonium× hortorum,* known as the variety Duefue, and hereinafter referred to by the cultivar name HWD Fuega.

The new cultivar is a product of a planned breeding program conducted by the inventor in Rheinberg, Germany. The objective of the breeding program was to develop a new dark-green foliage geranium with a unique purple red flower color.

The new cultivar originated from a cross made by the inventor of the nonpatented cultivar Monteverdi as the male or pollen parent with the patented cultivar Fiswig (U.S. Plant Pat. No. 7,385) as the female or seed parent.

The cultivar HWD Fuega was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Fuega. These characteristics in combination distinguish HWD Feuga as a new and distinct cultivar: 1. Semi-double rubine red flowers.

2. Large umbels.
3. Long peduncles.
4. Large flowers.
5. Compact plant size.
6. Dark green leaves.
7. Early flowering.

In comparison to the parent cultivar Monteverdi, plants of the new Geranium have semi-double flowers, dark green leaves, compact plant habit and flower earlier. In comparison to the parent cultivar Fiswig, plants of the new Geranium have rubine red (not carmine red) petal color, semi-double (not single) flowers, larger umbels, and flower earlier.

The new Geranium is similar in petal color to the patented cultivar Designer Rose (U.S. Plant Pat. No. 8,524) and the cultivars HWD Violetta and HWD Sorpresa (disclosed in the inventor's pending applications). In comparison to the cultivar Designer Rose, plants of the new Geranium have larger umbels, longer peduncles, more umbels per plant, larger flowers, and darker green foliage. In comparison to the cultivar HWD Violetta and HWD Sorpresa, plants of the new Geranium are more freely branching, more compact, and have larger umbels. Additionally, compared to HWD Violetta, plants of the new Geranium have smaller leaves, darker leaf color, larger flowers, and flower color is more red.

The accompanying colored photograph illustrates the overall appearance of the new cultivar, showing the colors as true as it is reasonably possible to obtain in colored reproduction of this type. Flower color appears more red than the actual flower color due to light reflectance. The photograph comprises a top perspective view of a typical potted plant of HWD Fuega with one plant in a 10-cm container.

The cultivar HWD Fuega has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal Geranium.

*Cultivar.*—*'HWD Fuega'.*

Parentage:

*Male parent.*—Nonpatented cultivar Monteverdi.

*Female parent.*—Cultivar Fiswag (U.S. Plant Pat. No. 7,385).

Propagation:

*Type cutting.*—Terminal cuttings.

*Time to initiate roots.*—Summer: 27° C., 21 days; winter: 20° C., 28 days.

Plant Description:

*General appearance.*—Rounded; compact plant size; upright; freely branching.

*Foliage description.*—Arrangement: Generally alternate. Shape: Orbicular with rounded tip and cordate base. Size: Length: 6.5 to 7.5 cm. Width: 7.5 to 8.5 cm. Texture: Velvety; pubescent on upper and under surfaces. Margin: Crenate. Color: Young foliage, upper surface: 147A. Young foliage, under surface: 147B Mature foliage, upper surface: Darker than 147A/139A. Mature foliage, under surface: 147A. Zone, upper surface: None. Zone, under surface: None. Veins upper surface; 146D, not prominent. Veins, under surface: 147C. Venation pattern; Palmate. Petiole: Length: 8 to 10 cm. Diameter: 2.5 to 3.5 mm.

*Stem description.*—Internode length: 1 to 1.5 cm.

*Lateral branch number:* 10 to 12. Lateral branch length: 6 to 8 cm.

Flowering Description

*Flowering habit.*—Freely flowering. Flowers arranged in umbels

Natural flowering season.—Year-round.

*Flowers borne.*—Flower buds develop in apical leaf axils. Umbels are displayed above the foliage.

*Quantity of inflorescences.*—Very floriferous; usually 8 open umbels and at least 7 developing umbels per plant at one time.

*Umbels.*—Form: Rounded. Diameter: 14 cm. Depth (height): 10 cm.

*Flowers.*—Form: Semi-double. Shape: Rounded. Quantity of flowers per umbel: 22. Diameter: 5 to 5.8 cm. Depth (height): 2 cm.

Petals.—Shape: Obovate with rounded tip. Arrangement: Rosette, overlapping. Quantity: 6 to 7. Aspect: Flat. Size: Length: 2.5 to 3 cm. Width: 2.1 to 2.5 cm. Texture: Satiny, smooth. Margin: Entire. Color: When opening, upper surface: 57A. When opening, under surface: 57A. Upper surface: More red than 57A. Under surface: 50A. Fading to, upper surface: 40D. Fading to, under surface: No fading observed.

*Petaloids.*—Shape: Irregular, generally obovate with rounded or clefted tip. Arrangement: Rosette, overlapping. Quantity: 3 to 5. Size: Length: 1.4 to 2.5 cm. Width: 0.5 to 1.5 cm. Texture: Satiny, smooth. Margin: Generally entire. Color: When opening, upper surface: 57A. When opening, under surface: 50A. Upper surface: More red than 57A. Under surface: 50A. Fading to, upper surface: 40D. Fading to, under surface: No fading observed.

*Peduncle (umbel stem).*—Angle: Erect, rigid. Length: 15 cm. Pubescence: Very fine, sparse. Color: 146C.

*Pedicel (individual flower stem).*—Angle: Erect, rigid. Length: 3 to 3.5 cm. Pubescence: Very fine. Color: 53A near sepals, gradually fading to 175A with hints of 147A at peduncle.

*Flower bud.*—Shape: Ovoid. Length: 1.3 to 1.5 cm. Diameter: 8 to 10 mm. Color: 43A/44A.

*Sepals.*—Arrangement: Rosette. Quantity: 5. Size: Length: 1 to 1.2 cm. Width: 4 to 5 mm. Shape: Acuminate with apiculate tip. Texture: Velvety. Margine: Entire. Color: Upper surface: 153A at base fading to 144A at tip. Under surface: 183B at base fading to 144A at tip.

*Reproductive organs.*—Androecium: Stamen number: 12. Anther size: 2 mm. Anther color: 61A. Pollen color: 32A. Gynoecium: Pistil number: 1. Pistil length: 1.1 cm. Stigma shape: Decurrent. Stigma color: 61B. Style length: 6 mm. Style color: 61B.

*Ploidy level.*—Tetraploid.

Disease resistance: No fungal, bacterial nor viral problems observed.

Seed development: Seed production is very rarely observed.

It is claimed:

1. A new and distinct cultivar of Geranium plant named HWD Fuega, as illustrated and described.

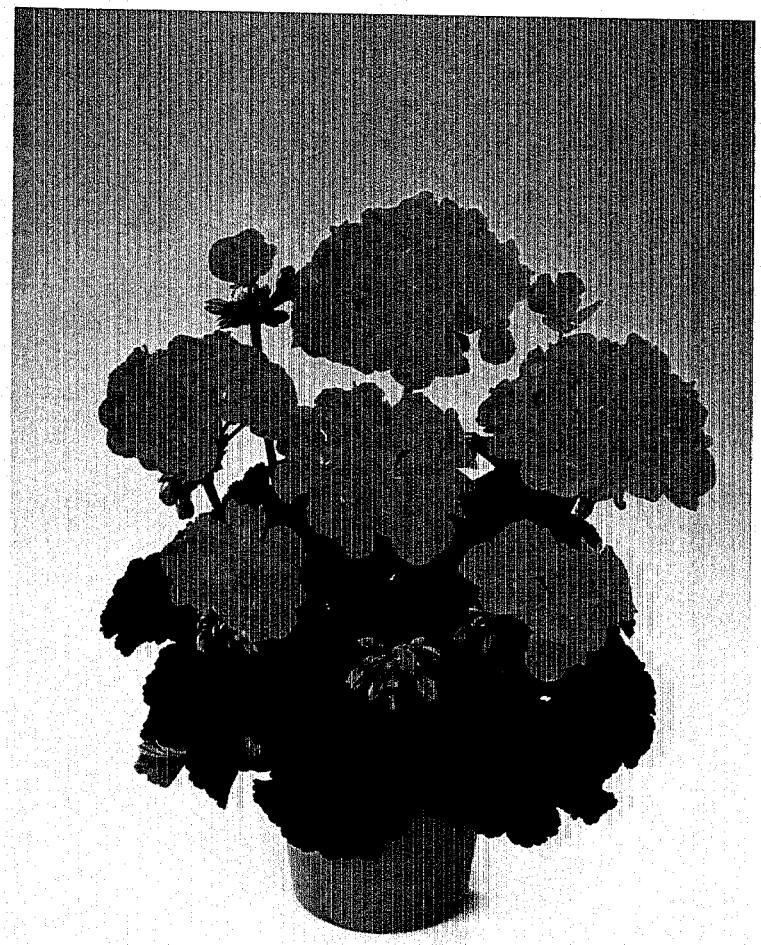

* * * * *